US00PP29488P2

(12) United States Plant Patent
Tuinier

(10) Patent No.: US PP29,488 P2
(45) Date of Patent: Jul. 10, 2018

(54) ***GASTERIA* PLANT NAMED 'D TIGA'**

(50) Latin Name: ***Gasteria* hybrid**
Varietal Denomination: D Tiga

(71) Applicant: Wander Durk Tuinier, Krimpen aan den IJssel (NL)

(72) Inventor: Wander Durk Tuinier, Krimpen aan den IJssel (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/530,821

(22) Filed: Mar. 3, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — C. A. Whealy

(57) ABSTRACT

A new and distinct cultivar of *Gasteria* plant named 'D Tiga', characterized by its upright rosette growth habit; dark green-colored leaves with numerous light green-colored tubercles; and excellent interiorscape performance.

2 Drawing Sheets

Botanical designation: *Gasteria* hybrid.
Cultivar denomination: 'D TIGA'.

BACKGROUND OF THE INVENTION

The present invention relates to a new and distinct cultivar of *Gasteria* plant, botanically known as *Gasteria* hybrid and hereinafter referred to by the name 'D Tiga'.

The new *Gasteria* plant is a naturally-occurring whole plant mutation of *Gasteria* hybrid 'WT10', disclosed in U.S. Plant Pat. No. 23,622. The new *Gasteria* plant was discovered and selected as a single plant within a population of plants of 'WT10' in a controlled greenhouse environment in Amposta, Catalonia, Spain in May, 2013.

Asexual reproduction of the new *Gasteria* plant by leaf cuttings in a controlled greenhouse environment in Amposta, Catalonia, Spain since March, 2014 has shown that the unique features of this new *Gasteria* plant are stable and reproduced true to type in successive generations.

SUMMARY OF THE INVENTION

Plants of the new *Gasteria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'D Tiga'. These characteristics in combination distinguish 'D Tiga' as a new and distinct *Gasteria* plant:

1. Upright rosette growth habit.
2. Dark green-colored leaves with numerous light green-colored tubercles.
3. Excellent interiorscape performance.

Plants of the new *Gasteria* differ primarily from plants of the mutation parent, 'WT10', in the following characteristics:

1. Leaves of plants of the new *Gasteria* are lighter green in color than leaves of plants of 'WT10'.
2. Leaves of plants of the new *Gasteria* have fewer tubercles than leaves of plants of 'WT10'.

Plants of the new *Gasteria* can be compared to plants of *Gasteria* hybrid 'Green Star', disclosed in U.S. Plant Pat. No. 24,763. Plants of the new *Gasteria* and 'Green Star' differ primarily in the following characteristics:

1. Plants of the new *Gasteria* are flatter than and not as upright as plants of 'Green Star'.
2. Plants of the new *Gasteria* have broader leaves than plants of 'Green Star'.
3. Plants of the new *Gasteria* and 'Green Star' differ in leaf color as leaves of plants of 'Green Star' are lighter green in color than leaves of plants of the new *Gasteria*.
4. Leaves of plants of the new *Gasteria* have more tubercles than leaves of plants of 'Green Star'.

Plants of the new *Gasteria* can also be compared to plants of *Gasteria* hybrid 'Royal Wolfgang', disclosed in U.S. Plant Pat. No. 25,667. Plants of the new *Gasteria* and 'Royal Wolfgang' differ primarily in the following characteristics:

1. Plants of the new *Gasteria* are flatter than and not as upright as plants of 'Royal Wolfgang'.
2. Plants of the new *Gasteria* have shorter and broader leaves than plants of 'Royal Wolfgang'.

BRIEF DESCRIPTION OF THE PHOTOGRAPHS

The accompanying colored photographs illustrate the overall appearance of the new *Gasteria* plant showing the colors as true as it is reasonably possible to obtain in colored reproductions of this type. Colors in the photographs may differ slightly from the color values cited in the detailed botanical description which accurately describe the colors of the new *Gasteria* plant.

The photograph on the first sheet comprises a side perspective view of a typical plant of 'D Tiga' grown in a container.

The photograph on the second sheet is a top perspective view of a typical plant of 'D Tiga' grown in a container.

DETAILED BOTANICAL DESCRIPTION

The aforementioned photographs and following observations, measurements and values describe plants grown during the early spring in 8.5-cm containers in a glass-covered greenhouse in Amposta, Catalonia, Spain and under cultural practices typical of commercial *Gasteria* production. During the production of the plants, day temperatures ranged from 20° to 25° C. and night temperatures ranged from 12° to 18° C. Plants were 20 weeks old when the photographs and description were taken. In the following description, color references are made to The Royal Horticultural Society Colour Chart, 2015 Edition, except where general terms of ordinary dictionary significance are used.

Botanical classification: *Gasteria* hybrid 'D Tiga'.

Parentage: Naturally-occurring whole plant mutation of *Gasteria* hybrid 'WT10', disclosed in U.S. Plant Pat. No. 23,622.

Propagation:

*Type*.—By leaf cuttings.

*Time to initiate roots, summer*.—About two weeks at temperatures about 20° C.

*Time to initiate roots, winter*.—About three weeks at temperatures about 20° C.

*Time to produce a rooted young plant, summer*.—About four weeks at temperatures about 20° C.

*Time to produce a rooted young plant, winter*.—About six weeks at temperatures about 20° C.

*Root description*.—Thick, fibrous; typically white in color, actual color of the roots is dependent on substrate composition, water quality, fertilizer type and formulation.

*Rooting habit*.—Freely branching; medium density.

Plant description:

*Plant form and growth habit*.—Herbaceous perennial plant; basal rosette plant form with upright leaves; flattened globular in overall shape; dark green-colored leaves with numerous light green-colored tubercles; low to moderate vigor and growth rate.

*Plant height*.—About 8.8 cm.

*Plant width*.—About 13 cm.

*Interiorscape performance*.—Plants of the new *Gasteria* have excellent interiorscape performance and have been observed to typically survive about two to three years in the interiorscape.

Leaf description:

*Arrangement and quantity*.—Leaves arranged in a basal rosette, simple, generally symmetrical and long-persisting; leaves sessile; about 28 leaves per rosette.

*Leaf length*.—About 8.3 cm.

*Leaf width*.—About 2.9 cm.

*Leaf thickness*.—About 7 mm.

*Tubercle height, upper surface*.—About 1.5 mm.

*Tubercle diameter, upper surface*.—About 1.5 mm.

*Tubercle height, lower surface*.—About 1 mm.

*Tubercle diameter, lower surface*.—About 1 mm.

*Leaf shape*.—Ovate.

*Leaf apex*.—Long apiculate with a mucronate tip.

*Leaf base*.—Broadly cuneate.

*Leaf margin*.—Sharply serrate.

*Leaf aspect*.—Flattened to slightly concave.

*Leaf texture, upper and lower surfaces*.—Glabrous; succulent; densely pustulate.

*Leaf luster, upper and lower surfaces*.—Moderately glossy.

*Leaf venation pattern*.—Not visible.

*Leaf color*.—Developing leaves, upper surface: Close to between NN137A and 139A; fading towards the base, close to 145C; margins, close to 147C; tubercles, close to 147B. Developing leaves, lower surface: Close to between NN137A and 139A; fading towards the base, close to between 150C and 150D; margins, close to 147C; tubercles, close to between 138B and 147B. Fully expanded leaves, upper surface: Slightly darker than between 139A and 147A; fading towards the base, close to 157D; margins, close to 147C; tubercles, close to 147B. Fully expanded leaves, lower surface: Slightly darker than between 139A and 147A; fading towards the base, close to 157D; margins, close to 147C; tubercles, close to between 138B and 147B.

Flower description: Flower initiation and development have not been observed to date on plants of the new *Gasteria*.

Disease & pest resistance: Plants of the new *Gasteria* have not been noted to be resistant to pathogens and pests common to *Gasteria* plants.

Temperature tolerance: Plants of the new *Gasteria* have been observed to tolerate temperatures ranging from about 5° C. to about 40° C. and to be suitable for USDA Hardiness Zones 10 to 12.

It is claimed:

1. A new and distinct *Gasteria* plant named 'D Tiga' as illustrated and described.

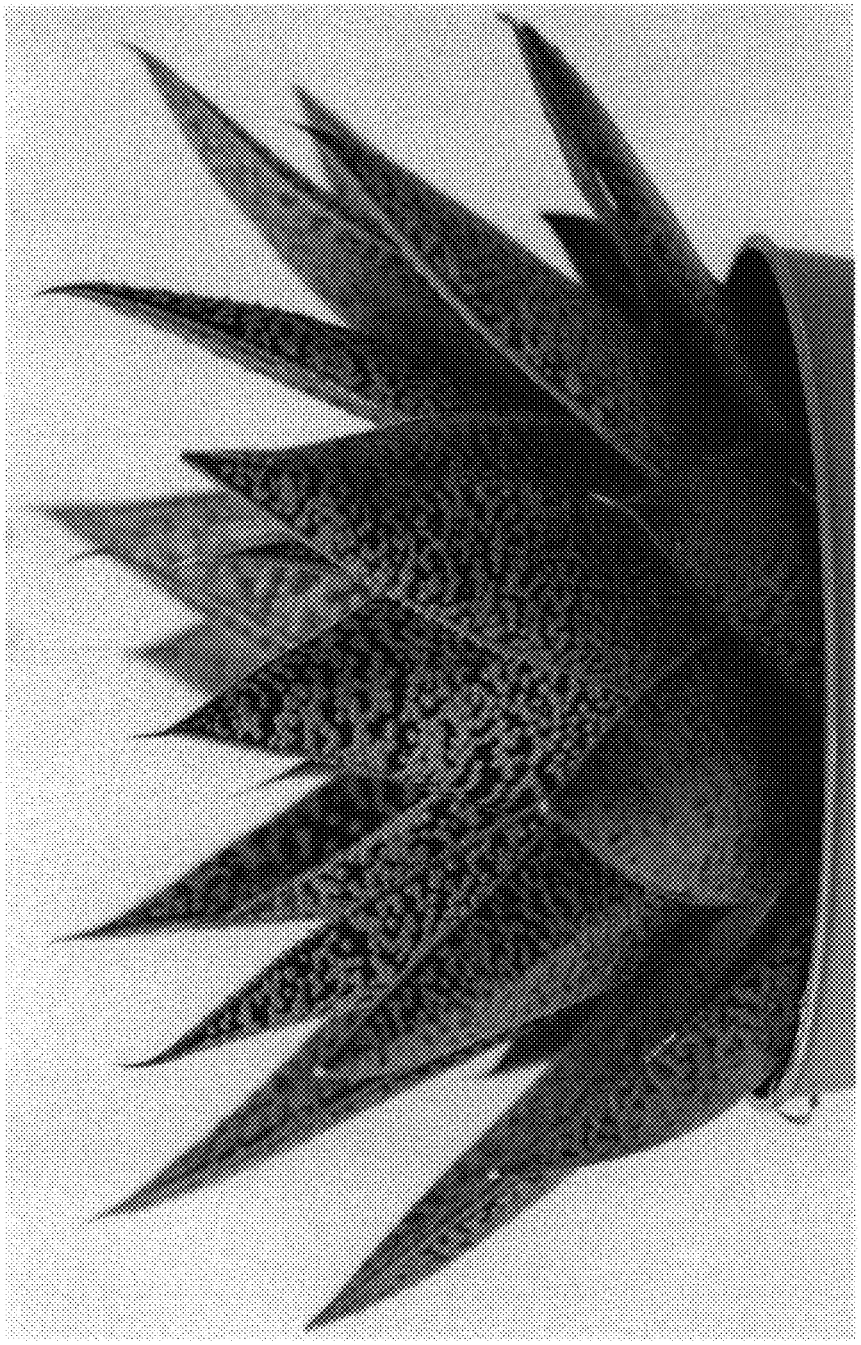

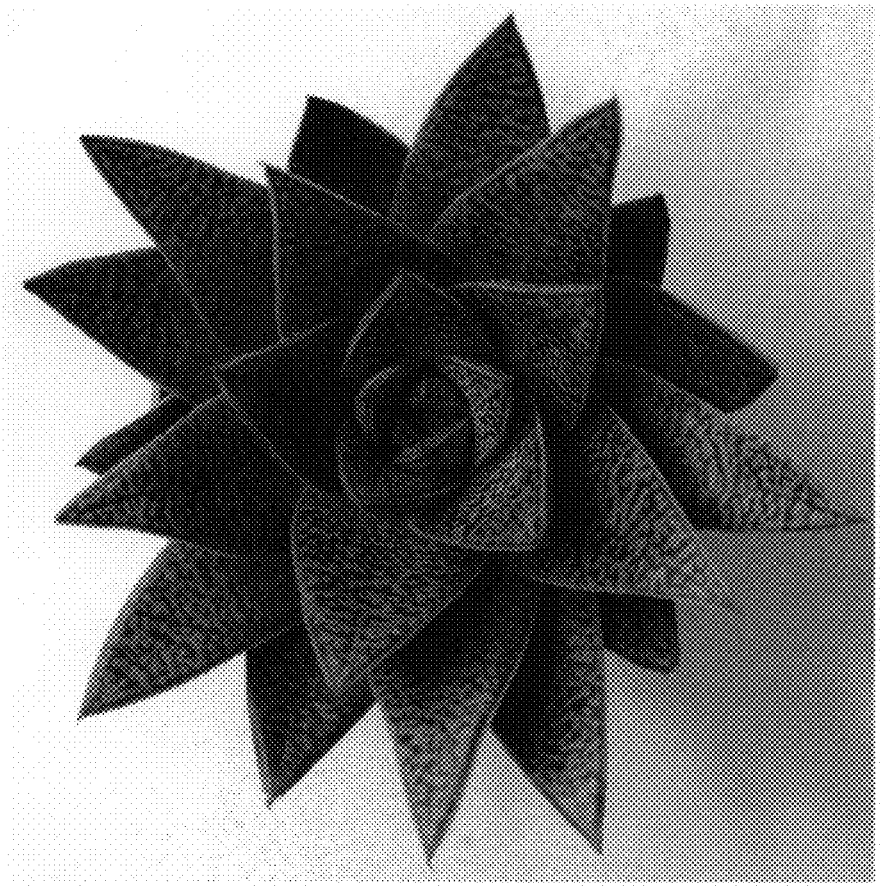

* * * * *